(12) United States Patent
Bondavalli et al.

(10) Patent No.: US 8,115,198 B2
(45) Date of Patent: Feb. 14, 2012

(54) ARRAY OF DIFFERENTIATED FETS HAVING A NANOTUBE OR NANOWIRE CHANNEL AND CORRESPONDING ELECTRONIC DEVICE, FOR THE DETECTION OF ANALYTES

(75) Inventors: Paolo Bondavalli, Paris (FR); Pierre Legagneux, Le Mesnil Saint Denis (FR); Pierre Le Barny, Orsay (FR); Didier Pribat, Sevres (FR); Julien Nagle, Palaiseau (FR)

(73) Assignee: Thales and Ecole Polytechnique (FR)

( * ) Notice: Subject to any disclaimer, the term of this patent is extended or adjusted under 35 U.S.C. 154(b) by 642 days.

(21) Appl. No.: 11/916,161

(22) PCT Filed: May 24, 2006

(86) PCT No.: PCT/EP2006/062615
§ 371 (c)(1),
(2), (4) Date: Nov. 30, 2007

(87) PCT Pub. No.: WO2006/128828
PCT Pub. Date: Dec. 7, 2006

(65) Prior Publication Data
US 2008/0210987 A1    Sep. 4, 2008

(30) Foreign Application Priority Data
May 31, 2005  (FR) ...................... 05 05492

(51) Int. Cl.
*H01L 51/10* (2006.01)
*H01L 51/30* (2006.01)
*H01L 27/105* (2006.01)
*H01L 27/28* (2006.01)
*H01L 29/43* (2006.01)
*H01L 29/78* (2006.01)

(52) U.S. Cl. .................. 257/40; 257/253; 257/E51.006; 257/E51.04; 257/E27.06; 257/E27.117; 257/E29.07; 257/E29.15; 977/920; 977/957

(58) Field of Classification Search ............ 257/40, 257/213, 252, 253, 613, 798, E51.001–E51.007, 257/E51.011, E51.023, E51.038, E51.039, 257/E51.04, E29.068, E29.069, E29.07, E29.071, 257/E29.111, E29.112, E29.113, E29.116, 257/E29.139, E29.15, E29.226, E29.242, 257/E29.245, E27.001, E27.01, E27.046, 257/E27.059, E27.06, E27.117; 977/902, 977/904, 920, 921, 932, 936, 938, 953, 957, 977/958
See application file for complete search history.

(56) References Cited

U.S. PATENT DOCUMENTS
7,214,553 B2    5/2007    Legagneux et al.
(Continued)

FOREIGN PATENT DOCUMENTS
DE    10331299    2/2005
(Continued)

OTHER PUBLICATIONS

Qi et al. "Toward Large Arrays of Multiplex Functionalized Carbon Nanotube Sensors for Highly Sensitive and Selective Molecular Detection", NanoLetters, 2003, vol. 3, No. 3, pp. 347-351.*

(Continued)

*Primary Examiner* — Lynne Gurley
*Assistant Examiner* — Andrew O. Arena
(74) *Attorney, Agent, or Firm* — Lowe Hauptman Ham & Berner, LLP (57) ABSTRACT

In an array R of field-effect transistors for detecting analytes, each transistor of the array comprises a gate G, a semiconductor nanotube or nanowire element NT connected at one end to a source electrode S and at another end to a drain electrode D, in order to form, at each end, a junction $J_1$, $J_2$ with the channel. At least transistors $FET_{1,1}$, $FET_{1,2}$ of the array are differentiated by a different conducting material ($m_1$, $m_2$) of the source electrode S and/or drain electrode D.

19 Claims, 8 Drawing Sheets

U.S. PATENT DOCUMENTS

| | | |
|---|---|---|
| 2003/0089899 A1 | 5/2003 | Lieber et al. |
| 2004/0001778 A1 | 1/2004 | Chen et al. |
| 2005/0053525 A1 | 3/2005 | Segal et al. |
| 2005/0235906 A1 | 10/2005 | Legagneux et al. |

FOREIGN PATENT DOCUMENTS

| | | |
|---|---|---|
| WO | WO02095099 | 11/2002 |
| WO | 2005048350 | 5/2005 |

OTHER PUBLICATIONS

Chen et al., "Noncovalent functionalization of carbon nanotubes for highly specific electronic biosensors", PNAS, vol. 100, No. 9, pp. 4984-4989 (2003).

Qi et al., "Toward large arrays of multiplex functionalized carbon nanotube sensors for highly sensitive and selective molecular detection", American Chemical Society Nano Lett., pp. A-E (2003).

Applicants List of Related Cases.

* cited by examiner

| $M_{EC}$ | | | |
|---|---|---|---|
| $(V_{th},g)_{1,1}$ | $(V_{th},g)_{1,2}$ | $(V_{th},g)_{1,3}$ | $(V_{th},g)_{1,4}$ |
| $(V_{th},g)_{2,1}$ | off | $(V_{th},g)_{2,3}$ | $(V_{th},g)_{2,4}$ |
| $(V_{th},g)_{3,1}$ | $(V_{th},g)_{3,2}$ | off | $(V_{th},g)_{3,4}$ |
| off | $(V_{th},g)_{4,2}$ | $(V_{th},g)_{4,3}$ | $(V_{th},g)_{4,4}$ |

FIG.7a

| R | | | |
|---|---|---|---|
| $FET_{1,1}$ | $FET_{1,2}$ | $FET_{1,3}$ | $FET_{1,4}$ |
| $FET_{2,1}$ | $FET_{2,2}$ | $FET_{2,3}$ | $FET_{2,4}$ |
| $FET_{3,1}$ | $FET_{3,2}$ | $FET_{3,3}$ | $FET_{3,4}$ |
| $FET_{4,1}$ | $FET_{4,2}$ | $FET_{4,3}$ | $FET_{4,4}$ |

ARRAY OF DIFFERENTIATED FETS HAVING A NANOTUBE OR NANOWIRE CHANNEL AND CORRESPONDING ELECTRONIC DEVICE, FOR THE DETECTION OF ANALYTES

CROSS-REFERENCE TO RELATED APPLICATIONS

The present Application is based on International Application No. PCT/EP2006/062615, filed on May 24, 2006, which in turn corresponds to France Application No. 05 05492, filed on May 31, 2005, and priority is hereby claimed under 35 USC §119 based on these applications. Each of these applications are hereby incorporated by reference in their entirety into the present application.

FIELD OF THE INVENTION

The present invention relates to sensors which are used for detecting analytes, in a gaseous or liquid environment, and which use, as transducer, one or more elements of the semiconductor nanotube type or semiconductor nanowire type.

It will be recalled that one difference between a nanotube and a nanowire is that the first is hollow and the other solid. They are elements having equivalent diameters, of the order of 1 nanometer or a few nanometers. Their diameter is small compared to their length.

The invention applies to the detection of particular species present in a specific environment, such as an urban environment (for example in a subway), in an industrial environment (laboratory room), a liquid medium (biochemical detection), etc. The analytes detected may be particular chemical or biological species, proteins, enzymes or other species, the harmfulness (virus, toxic gas, etc.) of which it is generally desired to detect.

To give an example, in many fields of industry (agrifood, pharmacy, etc.), in the field of industrial or civil security and prevention (domestic pollution) and in the military field, sensors are used for detecting an anomalous concentration of defined analytes in the medium under observation so as to prevent their hazardous effects, for example explosion, poisoning or contamination. In the biological field, this involves for example detecting certain toxins that may be dangerous, such as certain bacterial toxins, such as anthrax bacilli, or botulinum toxins, or certain viruses, such as for example smallpox, influenza, etc. In the chemical field this may for example involve detecting certain organophosphorus derivatives (sarin, tabun, etc.) and TNT, the danger of which is well known.

For these purposes, chemical sensors or biosensors are used. A biochemical sensor is a system that uses chemical reactions to detect an analyte. It creates a link between the chemical recognition element, which reacts with the analyte, and a transducer which links this chemical recognition to a useful physical signal and converts this physical signal into an electrical signal.

DESCRIPTION OF THE PRIOR ART

It is known to use semiconductor nanotubes as transducers, for example carbon nanotubes, for the purpose of detecting particular analytes. Indeed, it has been demonstrated that the electrical conduction properties of semiconductor nanotubes are very sensitive to the environment of these nanotubes. More particularly, the surface adsorption by a nanotube of molecules present in solution or gas molecules causes a significant variation in its electrical properties.

Sensors based on semiconductor nanotubes for example have been developed, particularly sensors that use a nanotube field-effect transistor as electronic detection element. These transistors are usually denoted by the acronym NTFET. The channel is formed by one or more nanotubes (2D array of nanotubes, etc.), for example one or more carbon nanotubes of the semiconductor type. In general, the carbon nanotubes are of the SWNT (single-walled nanotube) type.

The sensors using these transistors have proved to be very sensitive. However, they suffer from a lack of selectivity, which limits their capability of identifying a specific analyte in a mixture. For example, it is difficult for them to recognize a gas molecule in a gas mixture, or a specific protein in a mixture in solution. The problem is exacerbated if the composition of the mixture varies over the course of time. This may for example be the case in an urban environment, for example in a subway. This is because the cleaners use substances that emit particular gaseous effluents that act temporarily on the composition of the environment. The change over time may also involve a higher or lower humidity and thus may modify the composition of the atmosphere. If a detector for detecting a dangerous gas, such as sarin, is used in such an urban environment, the detection of this gas must not be disturbed by the normal changes in the various atmospheric conditions due to changes in the weather, or due to human intervention: cleaning, diffusion of a deodorizer, etc As regards the recognition of proteins, the selectivity problem is exacerbated by the phenomenon called NSB (nonselective binding) which is tied up with the attachment of protein molecules to the carbon nanotubes because of their hydrophobicity, independently of their origin, and which leads to an irreversible change in the response of the biosensor.

To improve the selectivity of sensors based on carbon nanotubes, and in particular based on NTFET transistors, it is known to functionalize the nanotube. According to the prior art, carbon nanotube functionalization consists in adsorbing or attaching molecules to its surface, for example those deposited by spraying droplets. Such functionalization improves the selectivity of the sensor acting as a catalyst, and it allows detection of one specified analyte rather than another.

It has been shown, for example in the article by Shu Peng, et al, "*Towards large arrays of multiplex functionalized carbon nanotube sensors*" (Nano Letters Vol. 3, No. 3, 347-351, 2003), that by functionalizing the nanotube of a transistor with a layer of a suitable polymer, it is possible to enhance the effect of the interaction between gases and carbon nanotubes—the transistor may be made more sensitive to a specific gaseous species. In addition, the polymer layer deposited on a nanotube may make the latter insensitive to interaction with a given species. The article gives an example in which a nanotube is functionalized with a layer of polyethyleneimine: the transistor becomes very sensitive to the presence of nitrogen dioxide ($NH_2$) but insensitive to the presence of ammonia ($NH_3$). Conversely, functionalizing the nanotube with a layer of Nafion®, which is a derivative of Teflon®, results in the transistor becoming very sensitive to the presence of ammonia ($NH_3$), but insensitive to the presence of nitrogen dioxide (NH2). The authors thus suggest the possibility of reducing sensitive selective molecular detectors on this principle, using arrays of specifically functionalized FET transistors.

However, for recognizing a gas or a gaseous species, these techniques have disadvantages associated with the selectivity within a given family of gases. This is because a specific gas may be a donor or an acceptor depending on the way in which it acts on the conductivity of the nanotube. According to the measurements made, two gases with the same character (whether a donor or an acceptor) may induce the same effect if the detection system is not appropriately designed. This problem is accentuated by the change in real time of this mixture, especially for applications in an urban environment.

In the field of the detection of biochemical or bacteriological species, functionalization of the nanotubes is fundamental for protein molecule recognition in order to overcome the NSB (nonselective binding) already mentioned, which has the effect that protein molecules tend to become attached to the walls of the nanotube because of their hydrophobicity. This phenomenon definitely changes the response of the transistor. The same transistor, if it is not functionalized, cannot therefore be reused several times for detecting proteins. In addition, a reproducible result cannot be obtained in the case of a mixture of several molecules. Functionalization therefore has the function of acting as an inhibitor for the reaction of certain proteins with the nanotube, in order to allow the reaction of other proteins which, by interacting with the nanotube, change the characteristics of the transistor, and therefore enable them to be detected.

Moreover, it is known to functionalize a carbon nanotube of the SWNT (single-walled nanotube) type by attaching organic, covalent or non-covalent, molecules to its surface by suitable methods. There is therefore a sensitive layer on the nanotube, which promotes the immobilization of another molecule that it is desired to detect, such as a protein, a particular biochemical substance, or the like. This immobilization modifies the electrical properties of the nanotube, which allows the presence of the immobilized molecule to be detected. Such functionalization is for example described in the article by R. Chen et al., "*Noncovalent functionalization of carbon nanotubes for highly specific electronic biosensors*" (4984-4989 PNAS, April 209 2003, Vol. 100, No. °9) and in international patent application published under the number WO 02/095099.

Thus, it is known in the prior art to functionalize FET transistor nanotubes with polymers or other (biochemical, organic, etc.) substances so as to improve their sensitivity and/or their selectivity and promote the detection of gaseous molecules, protein molecules, etc.

These techniques based on transistors comprising nanotubes functionalized with polymers make it possible to achieve beneficial results in terms of sensitivity (a few ppb).

In the invention, the aim is to obtain a sensor that is both compact, sensitive, rapid and reliable and that allows operation in real time in an urban environment and at ambient temperature.

In the invention, a sensor is sought that does not pose maintenance problems.

Hitherto, the functionalization techniques indicated do not meet these requirements satisfactorily.

SUMMARY OF THE INVENTION

The subject of the invention is an electronic detector of significantly improved sensitivity, selectivity and response time, which can be used for the detection of particular analytes in media that are relatively complex and can vary over time.

The invention deals more particularly with FET transistors having a lateral configuration, with a back gate and a channel produced by a semiconductor nanotube element (for example a carbon nanotube) or by a semiconductor nanowire (for example silicon nanowire(s)). Detection takes place by exposing at least a part of the surface of the source/channel junction and/or the drain/channel junction to the medium in which detection takes place.

In the invention, it has been demonstrated that, depending on the conducting material employed for producing the source and drain electrodes of a transistor, the current response of the transistor is a function of the voltage applied between gas and source $[I_{ds}=f(V_{gs})]$ is different depending on the medium to which the junction surface is exposed. More particularly, the gate voltage threshold above which the transistor is turned on varies depending on the molecules present in the medium to which the transistor is exposed, and according to the electrometal employed. This variation is not linear.

According to the invention, this phenomenon is used as a technique to differentiate transistors. Two transistors are thus differentiated by selecting a different conducting material for the source or the drain electrodes for each transistor so that the electrical properties of their electrode/channel junctions are different. The two transistors thus differentiated have a different threshold voltage, which also depends on the molecules present in the medium. The threshold voltage varies according to the type of junction and therefore according to the conductor material used to produce source/drain electrodes, and according to the molecules to which the junctions are exposed. Thus, depending on the gate-source voltage that is applied to the two transistors, and depending on the medium to which the junctions are exposed, one or both transistors are in the on-state, or one or both transistors are in the off-state. It will be recalled that the on-state or off-state of a transistor is usually detected by measuring the drain current of the transistor, generally denoted by $i_{ds}$.

Such a differentiation thus makes it possible to produce a specific imprint of the molecular composition of the medium in question. Using an array of differentiated transistors, comprising at least two differentiator transistors, but ideally a large number of them, the threshold voltage of each transistor of the array is an element of this imprint. It will be understood that if in a complex medium a specific molecule makes its appearance, the imprint of the medium will be modified—threshold voltages will change. Such an intrusion can thus be detected. Furthermore a concentration measurement is given by the slope of the measured curve of the drain current ($I_{ds}$) as a function of the voltage $V_{gs}$ applied between the gate and the source.

The idea is thus to use an array of FET transistors the channels of which are produced by a semiconductor-type nanotube or nanowire element, comprising at least two transistors, in which at least two transistors are differentiated by the conducting material used to produce the source and/or drain electrode, and to measure, continuously or in sequence, the threshold voltage of each of the transistors of the array in order to update a matrix of conduction states of the transistors of the array. In this matrix, a conduction state of a transistor is defined by its threshold voltage. This continuously updated state matrix is compared with imprints of the medium, defining one or more normal compositions of this medium, for the purpose of detecting any change and of generating a corresponding alarm.

An electronic device comprising an array according to the invention is both sensitive, selective and very quick to react. It is compatible with applications involving real-time detection/monitoring of media.

In particular, it allows a precise imprint of the characteristics of a medium to be produced in real time, according to the conduction state of the various transistors making up the sensitive array. By comparing this imprint with one or more reference imprints, typically obtained by calibration, it is possible to recognize the intrusion of a specific analyte into this medium.

This detection is very sensitive, that is to say it allows the presence of an analyte in a very small concentration, of the order of 1 pph to be detected. Such detection has been shown to be also very selective by making a judicious choice of the differentiation metals. An electronic detection device according to the invention thus allows very reliable detection of the presence of a particular analyte, for example sarin in an urban environment: the device is capable of detecting this analyte even at very low concentration (sarin is harmful even at very low concentration) and with a very low false alarm rate. It applies to any field that requires monitoring, whether continuous or activated in the event of a warning. This may be both monitoring in an industrial environment, such as a refinery, or monitoring of the quality of a natural gas distribution network, in order to check its composition at any moment.

An electronic detection device using an array of transistors according to the invention can be obtained by various methods using all proven techniques for fabricating semiconductor transistors and nanotubes, standard transistor voltage control and current read devices, and data processing means. It is simple to produce and may be very compact. In particular, it may be produced in portable form.

The device may be improved, especially for detection in liquids or in very humid environments, by functionalizing the nanotubes with appropriately selected polymers, especially for preventing the NSB effect. An alternative to functionalization by polymers, in the case of use in a medium that may be very humid (but not a liquid), for example in monsoon or tropical regions, is to use the device in a hot operation mode, for example for operating at a temperature of around 100° C. to 200° C., which may be obtained by inappropriate heat levels. In this way, the detection medium is locally "dried", at least in the detection zone of the device. This solves the problem of parasitic measurements depending on the humidity.

An electronic detection device according to the invention offers many advantages. In particular, it allows a very precise "imprint" of the characteristics of a gas or of a bacterium to be produced, and it allows this imprint to be detected by means of a very compact and very sensitive device, with a very short response time. This is a fundamental requirement for combat weapon detectors.

As claimed, the invention therefore relates to an array of transistors for the detection of analytes, each transistor of the array comprising a gate, a source electrode and a drain electrode, said electrodes being formed in a conducting material, and a nanotube or nanowire semiconductor element forming a channel of the transistor, said element being connected at one end to the source electrode and at the other end to the drain electrode, said source electrode, or said drain electrode, respectively forming with the channel a first junction or a second junction respectively. Said array comprises at least two differentiated transistors that are differentiated by different conducting material for the source electrode and/or drain electrode, said transistors each including an exposed detection zone comprising one or both junctions from among the first and second.

The invention also relates to an electronic analyte detection device comprising such an array.

Still other objects and advantages of the present invention will become readily apparent to those skilled in the art from the following detailed description, wherein the preferred embodiments of the invention are shown and described, simply by way of illustration of the best mode contemplated of carrying out the invention. As will be realized, the invention is capable of other and different embodiments, and its several details are capable of modifications in various obvious aspects, all without departing from the invention.

Accordingly, the drawings and description thereof are to be regarded as illustrative in nature, and not as restrictive

DETAILED DESCRIPTION OF THE INVENTION

The invention relates to an array of transistors for detecting analytes. In these transistors, a nanotube or nanowire semiconductor element NT forms the channel of the transistor.

The semiconductor element is connected at its two ends to a source electrode and to a drain electrode. These two electrodes are made of a conducting material, typically metal. Thus, for each transistor, there is a source/channel junction and a drain/channel junction.

According to the invention, the modifications in the electrical properties of at least one of the source/channel or drain/channel junctions of the transistor, the surface of which, or at least part of it, is exposed to an analyte to be detected. This surface is preferably at least the source/channel junction.

The transistor used must therefore have a structure such that at least one junction with the channel, and preferably the junction associated with the source electrode, is exposed to the medium undergoing detection. The transistor is thus provided with an exposed detection zone comprising one or both junctions, which are thus placed in a condition for reacting with an environment, which may be liquid or gaseous.

Hereafter, for the purpose of simplifying the presentation, the invention is described in the case of a semiconductor nanotube transistor (for example a semiconductor carbon nanotube transistor).

The same properties and the same effects may be obtained by using, instead of one or more nanotubes, one or more semiconductor nanowires, this constituting a variant of the invention. The following description may be applied in an equivalent manner to this variant by replacing "carbon nanotube(s)" or "nanotube(s)" with nanowire(s).

Figure 1A:
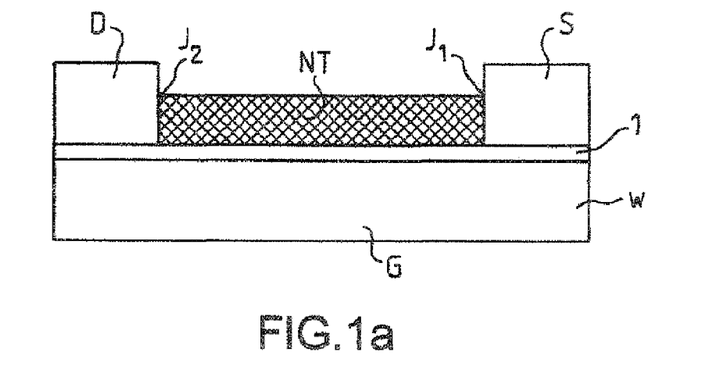
FIGS. 1a and 1b each show an NTFET transistor structure that can be used in the invention.
Figure 1B:
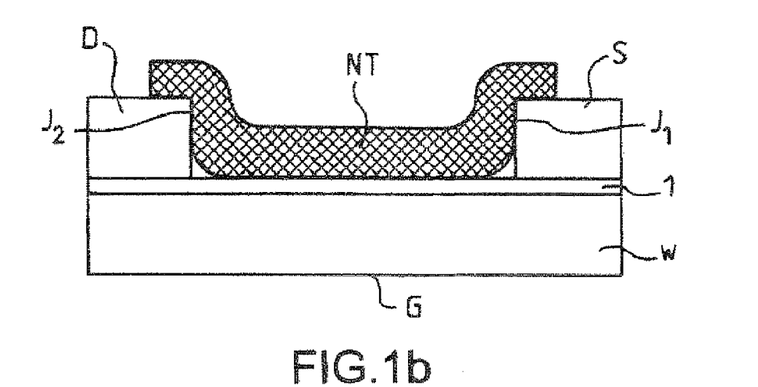

A structure of a transistor that can be used for a use according to the invention is illustrated in FIGS. 1a and 1b, in an example of a lateral configuration. In particular, the channel is formed by a semiconductor nanotube element. The transistor is a rear-gate transistor, so that the nanotube element and the source and drain electrodes based on the active face may be exposed to the medium it is desired to monitor. As illustrated in FIG. 2d, those parts of the active face that are not exposed are usually protected in FET transistor fabrication technology by at least one passivation layer cp. This passivation layer includes apertures corresponding to the free exposed surfaces of the array, that is to say the exposed detection zones of the transistors, by which the analytes will be detected.

In more detail, an FET transistor comprises a gate G, a source electrode S, a drain electrode D and a semiconductor nanotube element NT which joins the two—source and drain—electrodes and forms the channel of the transistor. The source electrode forms a first junction $J_1$ with a channel while the drain electrode forms a second junction $J_2$ with the channel.

In the example illustrated in FIGS. 1a and 1b, the gate G of the transistor is of the back gate type and formed by a semiconductor substrate w. A dielectric layer 1 is provided on the gate G.

The nanotube element NT is placed on this dielectric layer 1. In the example it is formed from a single nanotube.

The nanotube element NT may in practice be formed from a nanotube or from several nanotubes. In the latter case, the nanotubes may be organized in a parallel fashion, according to a 2D array, or may be linked together in series. The expression "nanotube element" used in the present description covers all these practical embodiments.

Two conducting electrodes produced on the dielectric layer 1 are based on either side of the nanotube element NT. One forms the drain D of the transistor and the other the source S. They are for example metal pads, in the form of mesas, obtained by depositing a layer of metal and then etching it. In another example, they are nanowires of conducting materials, which are suitably deposited.

Each of electrodes S and D is connected to one end of the nanotube element so as to form a junction with the channel at each end, namely the junction $J_1$ with the source electrode and the junction $J_2$ with the drain electrode.

The contact between each of the electrodes and one end of the nanotube element NT may in practice be obtained according to two different embodiments, depending mainly on whether the nanotube element is deposited before or after the electrodes.

This is what will be illustrated below by taking the example of electrodes formed by metal pads.

In a first embodiment illustrated in FIG. 1a, the electrodes are produced after the nanotube element NT has been deposited on the dielectric layer 1. For example, the electrodes are formed by deposition followed by self aligned etching on the nanotube element so that the junctions of the nanotube element with the electrodes lie in the plane of the nanotube element. This is the embodiment illustrated in FIG. 1a. The contact surface between the two materials forming the junction is essentially defined by the metal-covered surface of the nanotube.

In a second embodiment, illustrated in FIG. 1b, the source electrode S and drain electrode D are produced on the dielectric layer 1 (by deposition following by etching). The nanotube element NT is then deposited by partly covering the mesas of the electrodes. In this case, the contact surface between the two materials forming in each junction (metal/nanotube) is mainly the surface of the upper plane and of the sidewall of the mesa in contact with the nanotube element. This is the embodiment illustrated in FIG. 1b.

In the case in which the nanotube element is formed by a plurality of nanotubes, the nanotubes may contact the two electrodes or directly (2D array) or else by forming a chain, which enables them to be contacted, or else both.

It is in the region of the contact surface between the two materials of the junction that the dominant charge transfer mechanism takes place, and it is in this region that the analytes have the maximum influence.

Figure 2A:
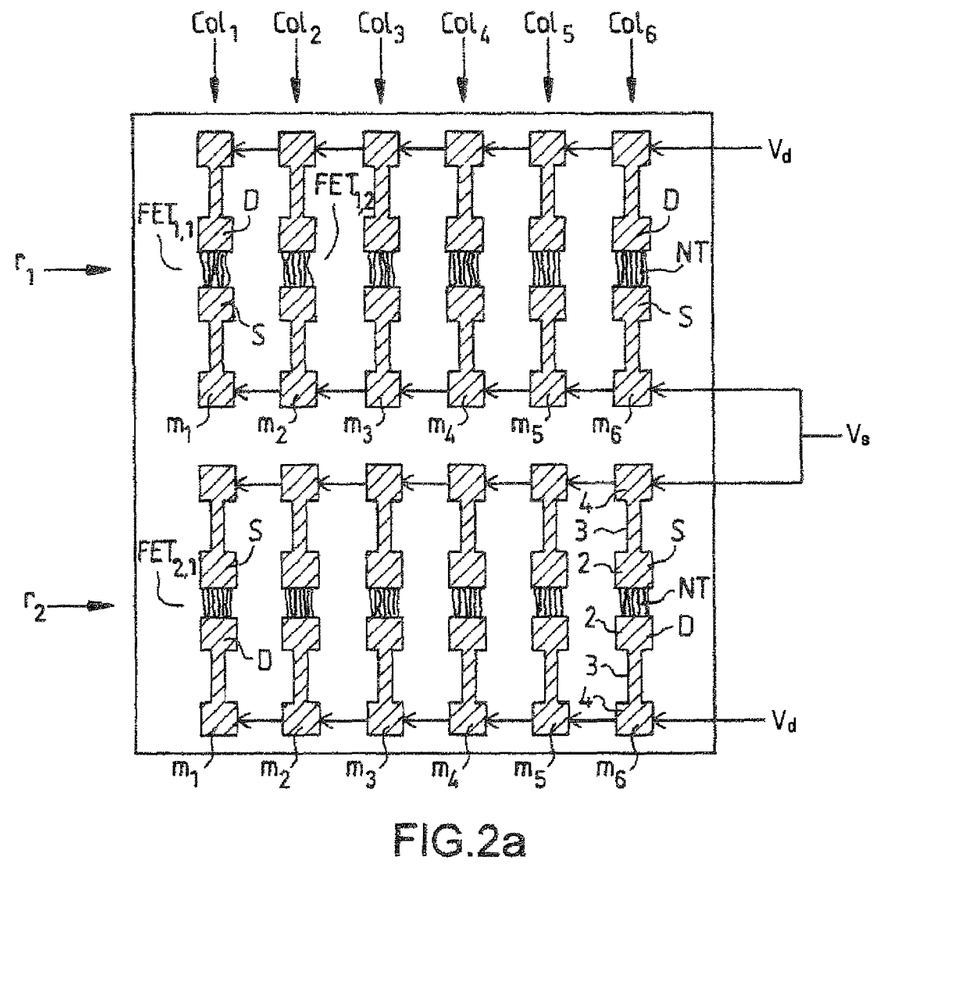
FIGS. 2a to 2d show a configuration of an array of differentiated transistors according to the invention, seen from above (FIGS. 2a and 2c) and in cross section along col.1 (FIGS. 2b and 2d)
Figure 2B:
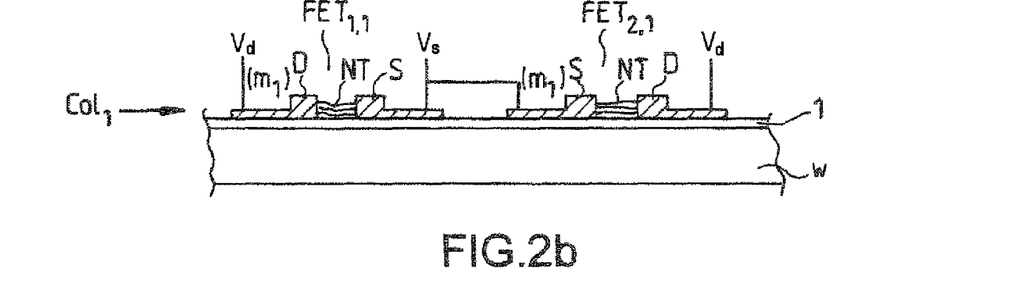

An array comprising a plurality of transistors of this type is illustrated in FIG. 2a (top view) and FIG. 2b (sectional view) in a first embodiment according to the invention.

The transistors are produced on the same semiconductor substrate w, which acts as gate G for each of the transistors of the array. In this embodiment and as demonstrated in FIGS. 2a and 2b, the source and drain mesas are extended by conducting tracks and terminate in contact pads.

The substrate is for example a p-type (i.e. p-doped) silicon substrate on which a thin layer of oxide $SiO_2$ has been deposited in order to form the dielectric layer 1 (FIG. 2b). Other oxides and types of substrate that produce the same functions and are technologically compatible may be used. The thickness of the oxide layer, the thickness of the wafer and its doping are in practice optimized according to the application.

In this embodiment, and as shown in FIGS. 2a and 2b, the source S and drain D electrodes each comprise a mesa 2, which forms the junction with the channel and is extended by a conducting track 3 that terminates in a contact pad 4. In practice, the mesa, the conducting track and the contact pad are generally produced in the same conducting material. Likewise, the source and drain electrodes of any one transistor are generally produced in the same conducting material for homogeneity and fabrication process simplification reasons.

According to the invention, at least some of the transistors of the array R are differentiated from other transistors of the array by the conducting material employed to produce their source and drain electrodes. Thus there is an array of differentiated transistors, the different responses according to the medium to which their junctions are exposed enabling a specific analyte to be detected.

The conducting material employed for each transistor is thus selected from a set of conducting materials compatible with the substrate w used. In one example in which the substrate used is a silicon substrate and the conducting material is a metal, this material is for example chosen from those of the following nonexhaustive list: TiW/C, Ti/Au, Cr/Au, Ti, Co, Au, Al, Pd, Pt, Ni, Mo, W, etc.

The array may comprise a number N of transistors which are all differentiated, or some of which are identical, that is to say not differentiated within the meaning of the invention. They may be arranged in any fashion, but it is preferred to arrange them in a row, and better still in a matrix fashion.

Such a matrix array is illustrated in FIG. 2a. The transistors are arranged in rows $r_1$, $r_2$ and columns $Col_1$, $Col_2$ ... to $Col_6$.

The differentiation of the transistors all produced on the same substrate assumes that there are as many deposition and edging steps as different conducting materials used. Preferably, for the sake of simpliciation and homogeneity, the source and the drain of any one transistor are preferably produced in the same metal. If, as in the example illustrated in FIGS. 2a and 2b, six differentiating conducting materials $m_1$, to $m_6$, are used, the corresponding fabrication process comprises six deposition/etching operations, one per differentiating material used. In the example, the transistor $FET_{1,1}$ (row $r_1$ and $Col_1$) and $FET_{1,2}$ (row $r_1$ and $Col_2$) are differentiated, the first being characterized by the conducting material $m_1$ and the second by the conducting material $m_2$; the transistors $FET_{1,1}$ (row $r_1$ and $Col_1$) and $FET_{2,1}$ (row $r_2$ and $Col_1$) are identical, both being characterized by the same conducting material $m_1$.

Figure 2C:
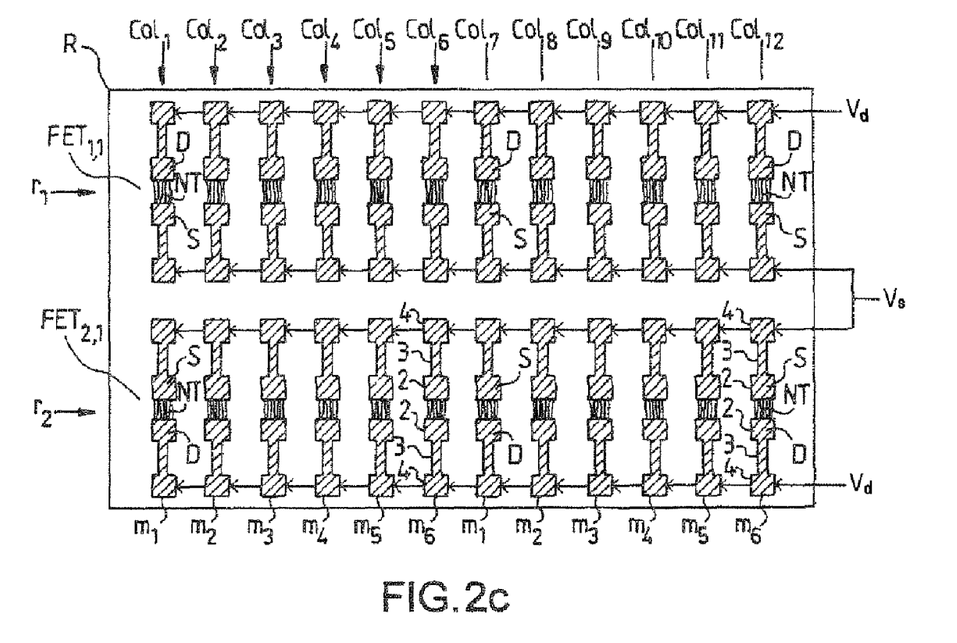
Figure 2D:
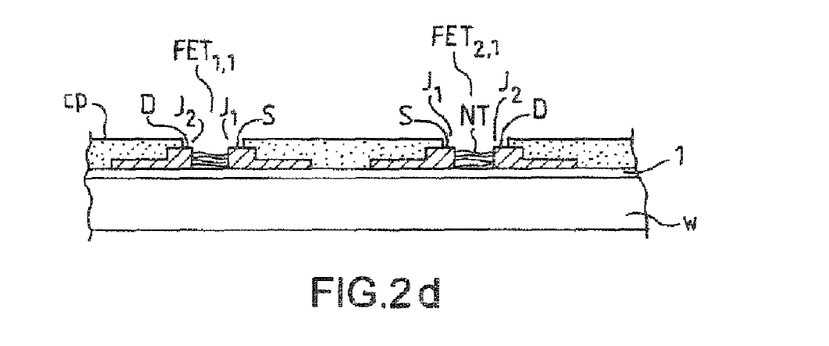

For the purpose of simplifying the fabrication of such an array, a linear differentiating "pattern" may be provided, for example a differentiating pattern that repeats itself from row to row, as illustrated in FIG. 2a. The row pattern is characterized by n transistors and n different metals; in the example, a conducting material $m_1$ for the transistors of column $Col_1$, a conducting material $m_2$ for the transistors of the column $Col_2$, etc., until a conducting material $m_6$ for the transistors of column $Col_6$. This differentiating pattern ($m_1$, $m_2$, $m_3$, $m_4$, $m_5$, $m_6$) is repeated from row to row. It may also be repeated periodically along the row. Thus, FIG. 2c shows two identical rows $r_1$, $r_2$ in an array with a repetition of the differentiating pattern ($m_1$, $m_2$, $m_3$, $m_4$, $m_5$, $m_6$), once along columns $Col_1$ to $Col_6$, and once along the following columns $Col_7$ to $Col_{12}$.

In an alternative embodiment (not shown), the pattern may be repeated from column to column. It is also possible to have a two-dimensional repeat pattern. Many combinations are thus possible, which will be determined according to the fabrication requirements, the performance characteristics, the applications, etc.

The repetition of a differentiating pattern, whether 1D or 2D or periodic, advantageously facilitates fabrication.

The use of several identical transistors, that is to say transistors produced with the same conducting electrode material, makes it possible to optimize the detection area for each "type" of transistor—its detection area is equal to the exposed area of the junctions $J_1$, $J_2$ of each transistor multiplied by the number of transistors of the same type.

Such an arrangement also has the advantage of offering the possibility of redundancy. For example, and as illustrated in FIG. 2a, a first row of transistors differentiated pairwise by the metal of their source and drain electrodes may be provided. The differentiation is illustrated by the various patterns of the electrodes. This row is duplicated by a second, identical row, which provides a redundancy function. In the case of one or more transistors of the first row failing, these transistors may be replaced with the identical transistors of the second row. Redundancy may also be provided along the columns. Alternatively, the redundancy may be provided along the row (or the column) itself using the following "pattern".

This redundancy may be used to limit the scrap rate during fabrication of the array, but also in operation, (dynamic redundancy) by providing suitable redundancy test and activation means.

It should be noted that the arrangement and the shape of the source and drain electrodes are indicative. They are chosen according to the technology used to allow better connection of the contact pads 4 for the source S and drain D (FIG. 2a) to the voltage supply buses that supply the voltage Vd and the voltage Vs to the drain D and to the source S respectively (FIG. 2b). These buses are produced in the usual way according to the state of the art.

Various electrode arrangements may be envisaged, such as for example the linear arrangement at the side of the channel, as illustrated in FIGS. 2a to 2c. In such an arrangement, the source and drain contacts are advantageously reversed, so that all the source contacts in the example are supplied by a supply bus for delivering the source voltage $V_s$ in the middle of the array and all the drain contacts are supplied by a supply bus for delivering the drain voltage $V_d$ said supply bus being placed on the periphery.

Figure 3:
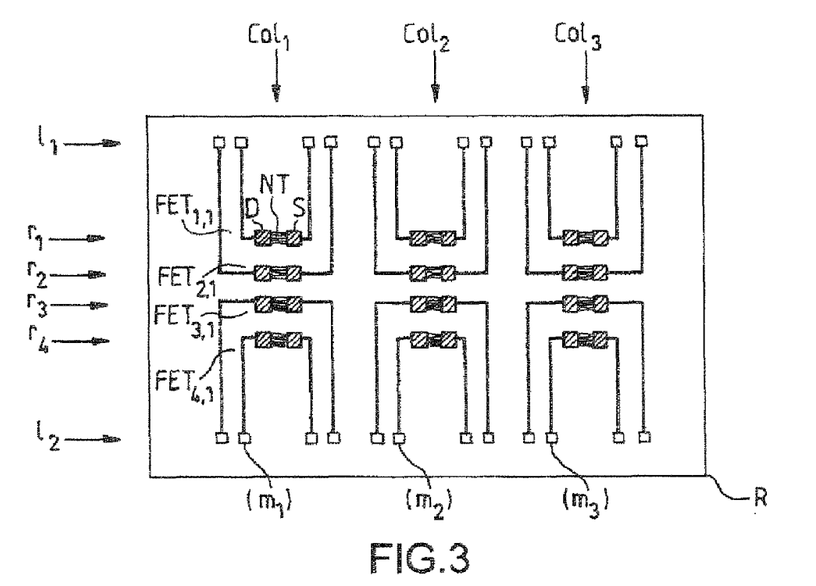
FIG. 3 shows another configuration of a differentiated array according to the invention.

Another arrangement is illustrated in FIG. 3. This is a U-shaped arrangement, bringing the source and drain contact pads of one or more lines along a parallel line. In the example, the source and drain contact pads of the transistors of rows $r_1$ and $r_2$ are aligned along a line l1, on the periphery of the array, and the source and drain contact pads of the transistors of rows $r_3$ and $r_4$ aligned on a line l2, on the periphery of the array.

In an alternative embodiment of the invention, the transistors are differentiated by varying the contact surface between the two materials forming the junctions. This involves varying the number of metal atoms available for contacting the semiconductor material. Such an embodiment makes it possible to simplify the fabrication of the array by reducing the number of differentiating metals used, without degrading the detection performance, especially in terms of noise.

Figure 8A:
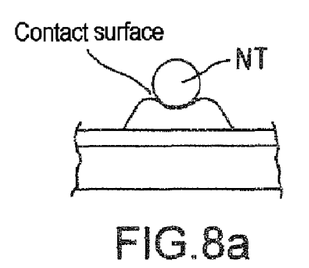
FIGS. 8a and 8b illustrate one embodiment of the transistor differentiation by the contact surface between the two materials of the junction.
Figure 8B:
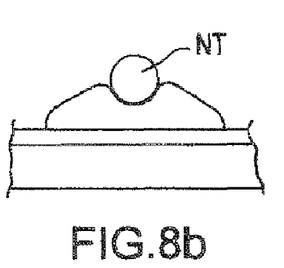

In a practical exemplary embodiment, the conducting material used for the electrodes may be varied in order to modify this contact surface. This is illustrated by way of example in FIGS. 8a and 8b. Depending on the transistor, a different amount of metal (or a different number of metal nanowires) is deposited, the nanotube element NT is deposited on top, and then an annealing operating is carried out. This results in different shapes and dimensions of the mesas—the contact surface between the conducting material and the semiconductor material may thus be modified from one transistor to another.

Figure 9:
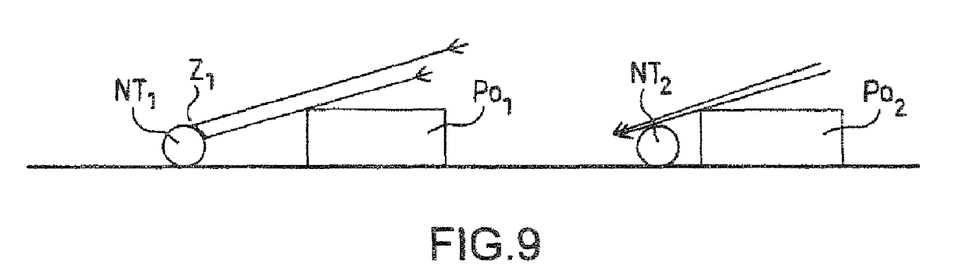
FIG. 9 illustrates an alternative embodiment of this differentiation by contact surface.

In another practical exemplary embodiment illustrated in FIG. 9, the nanotube element NT is deposited first, and then a mask is produced as active face, for example made of a resist or any other suitable material, with an appropriate design so as to form shadowing pads $Po_1$, $Po_2$ around the ends of the nanotube elements $NT_1$, $NT_2$, at a variable distance therefrom, depending on the transistors. A dielectric is then deposited using a directional process, at a raising angle. Thus, as illustrated in FIG. 9, a variable part of the surface of the nanotube may be covered with a dielectric according to the distance between the shadowing pad and the associated nanotube element. The nanotube element $NT_1$ is thus covered with a dielectric layer in a zone $Z_1$, whereas the other nanotube element receives no dielectric at all.

After this dielectric-based differentiating step, the source and drain electrodes partly covering the ends of the nanotube are produced so as to ensure contact therewith.

Where there is dielectric on the nanotube, this dielectric acts locally as passivation—there is no electrical contact in this zone between the two materials that form the junction. Thus, depending on the area of dielectric deposited, the shape and the dimensions of the contact surface of the junction are different. The electrical response of the transistor will therefore also be different, depending on the characteristics of the contact surface of the junction exposed to the analytes to be detected.

In another alternative embodiment of an array of transistors according to the invention, provision may be made to use a plurality of substrates, i.e. at least two substrates. Identical transistors are produced on each substrate. This makes it possible to have to use only one metal per substrate. The fabrication process is thereby simplified and the time required to fabricate a substrate is reduced. Next, the transistors coming from various substrates are assembled on a single support, to form an array of differentiated transistors according to the invention.

Figure 4A:
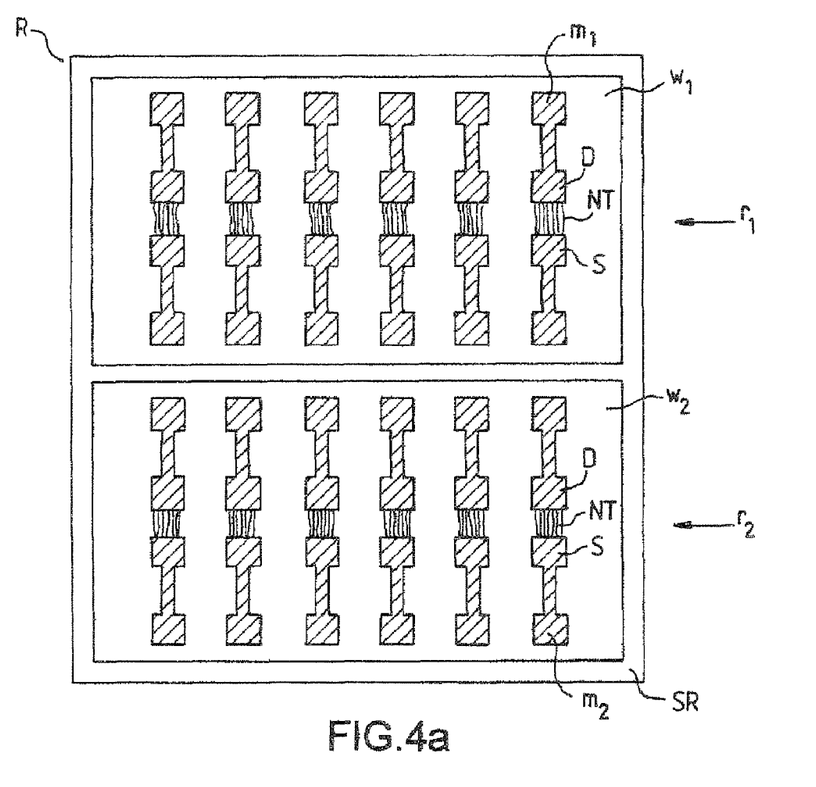
FIG. 4a illustrates a top view of another configuration of an array according to the invention, comprising an assembly of various substrates.
Figure 4B:
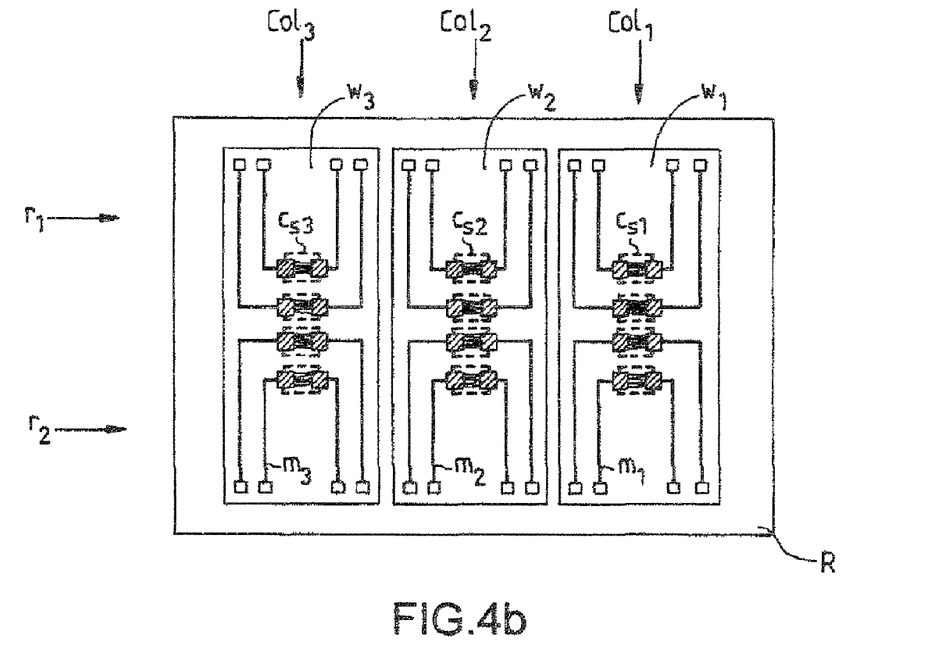
FIG. 4b illustrates, in top view, a variant of an assembly of substrates and functionalization of the transistors of the array with polymers.

An illustrative example of an array R according to this embodiment is shown in FIGS. 4a and 4b with metal electrodes. In the example illustrated in FIG. 4a, there are two substrates $w_1$ and $w_2$ placed in two parallel rows $r_1$ and $r_2$. A line of identical transistors is produced on each substrate. On the first substrate $w_1$, the source/drain electrodes are produced in a first metal $m_1$. On the second substrate $w_2$, the source/drain electrodes are produced in a second metal $m_2$.

FIG. 4b illustrates an alternative embodiment in which the various substrates, in the example $w_1$, $w_2$ and $w_3$, are placed along three parallel columns.

This method of assembling various substrates makes it possible to simplify the fabrication process, by paralleling the differentiation of the transistors—the transistors to be differentiated are produced on different substrates. A corresponding process will for example comprise the following steps:

The process starts with several substrate wafers. As many transistors as permitted by the technology are produced on each wafer. These transistors are all identical on a wafer and characterized by a specific electrode material.

Thus, as many transistor wafers as different metals permitted for a given technology (for example p-type silicon substrate) may thus be produced.

Next, the wafers are cut up into transistor sub-assemblies so as to form identical transistor subarrays.

Chosen subarrays are then assembled in a suitable manner according to their differentiating metal on a given support SR.

For example, n subarrays $w_i$, are selected, each subarray being characterized by a given metal $m_i$, where i=1 to n, and they are assembled on a given support, so as to form an array according to the invention. It is possible to select the subarrays and to assemble them in various ways. In particular, it may be desirable to have more transistors of one type than of another, to distribute them in rows, or in columns, or in both, etc. according to various technological or use criteria. Depending on the configuration chosen, the subarrays will be 1D or 2D subarrays. The invention is not limited to one particular array configuration.

In the example shown in FIG. 4a, there are two 1D subarrays $w_1$ and $w_2$ placed in parallel where each forms a row $r_1$, $r_2$ of the array, on a support SR. The transistors of the subarray $w_1$ forming the row $r_1$ have their source S and drain D electrodes made in a first metal $m_1$. The transistors of the subarray $w_2$ forming a row $r_2$ have their source S and drain D electrodes made in another metal $m_2$.

This makes it possible to use a wide palette offered by a given technology in the choice of metals or even of the substrates, without encountering problems of limitation due to their compatibility and those due to the degree of production complexity (in particular, the number of steps in the process).

Various solutions may be provided for electrically connecting the sources, drains and gates of all these transistors.

Figure 4C:
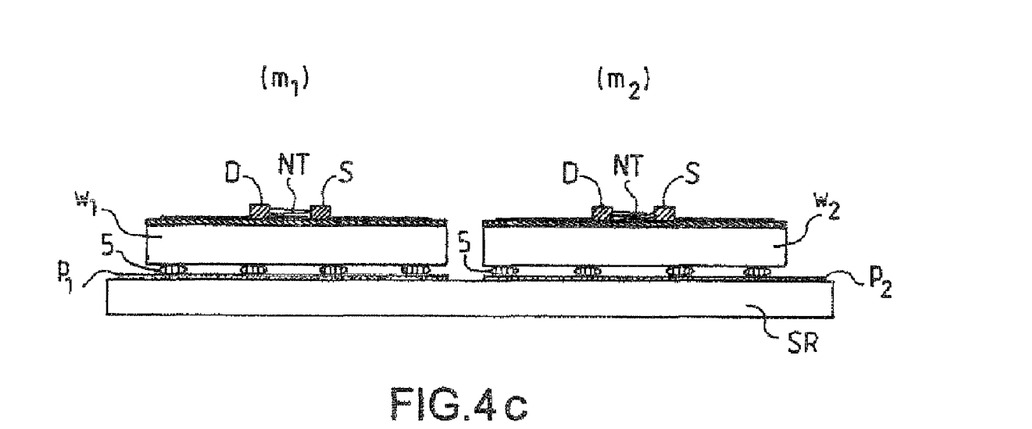
FIGS. 4c and 4d are corresponding sectional views of FIGS. 4a and 4b.

Advantageously, and as shown in FIG. 4c, the array support SR on which the n subarrays are placed is provided with an array of conducting tracks $p_1$, $p_2$, which will make it possible, by mounting the subarrays on this support using a flip-chip technique, to apply an appropriate gate voltage to each of the gates of the transistors of the array.

In an advantageous configuration, each subarray is provided on its back face, on the substrate, with conducting balls 5 or pellets which also serve as attachment means (conductive adhesive). These balls are mounted on the support SR on a conducting track such as the track $p_1$ in the figure, which serves as plane for supplying the gates of the transistors of the subarray that is mounted thereon.

Figure 5:
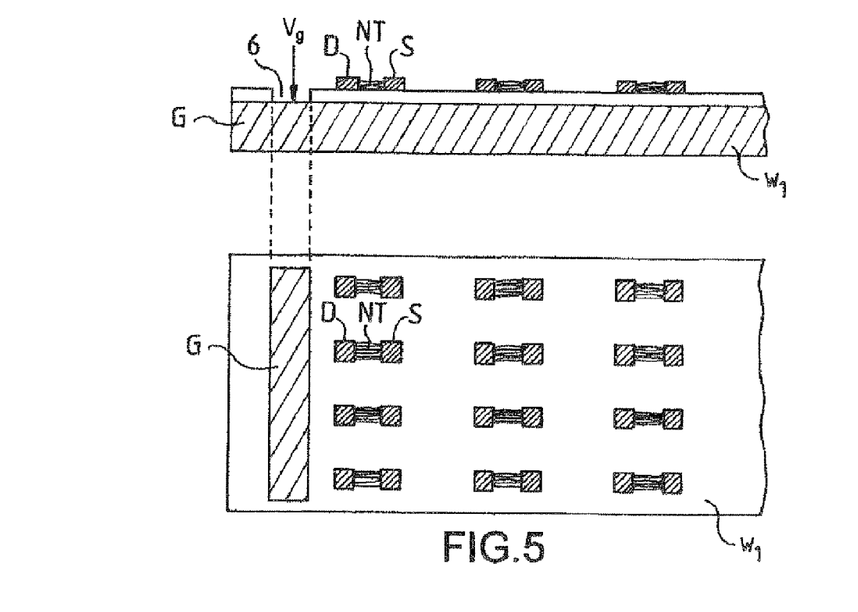
FIG. 5 illustrates one embodiment of the gate connection for applying the necessary control voltage.

In another configuration, shown in FIG. 5, the gate contact on the active face of the substrate w (FIG. 2a) or of each subarray $w_1$ (FIG. 4a) is produced. The gate contact G of each subarray $w_1$ (or substrate) is then produced on the active face by etching the dielectric layer 1 until reaching the substrate, in order to form a via 6 to which the gate voltage $V_g$, will be applied, typically by a supply bus (not shown). The transistors of any one subarray will preferably have their gates connected in common to the same gate voltage. Provision may thus be made for all the transistors of all the subarrays to have their gates connected in common to the same gate voltage.

In an improvement of the invention, to improve the selectivity of the detection transistor array thus produced, the nanotube element NT of all or some of the transistors of the array may furthermore be functionalized by producing a sensitive layer on the nanotube element NT, which may be a layer of polymer, of enzymes or of other chemical substances. In this way, the selectivity of the detection device is improved and the NSB problem in the case of protein recognition is avoided. The transistors thus become more sensitive to variations in analyte concentrations.

This improvement applies to the various alternative configurations of an array according to the invention. The sensitive layer placed on the transducer nanotobe element NT may be a layer of a specific polymer, or more generally a layer of molecules chosen for their capability of capturing, immobilizing and adsorbing specific analytes that it is desired to detect, the presence of which layer will modify the response of the transducer. This may be a layer of a complex chain of molecules, a layer of polymer, a layer of enzymes, a layer of proteins, etc.

Figure 4D:
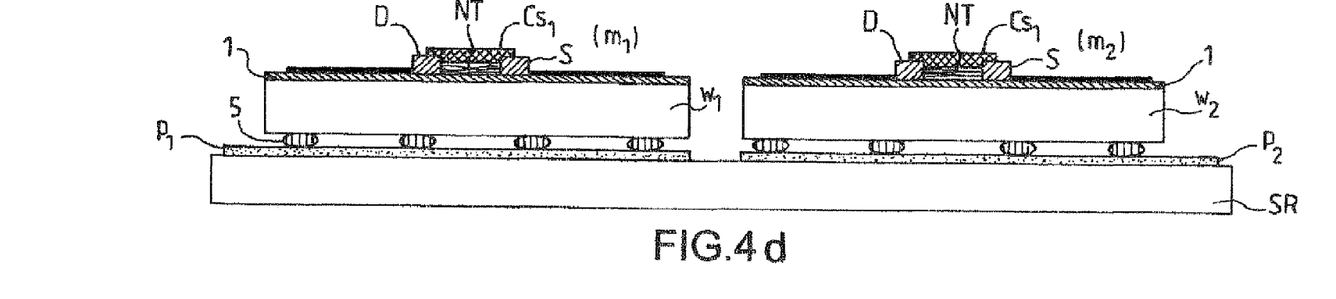

As illustrated for example in FIGS. 4b and 4d, the nanotube element NT of one transistor, or of several transistors or of all the transistors, of the array R is thus covered with a sensitive layer, which may vary from one transistor to another. In the example shown in FIG. 4b, there is thus a specific sensitive layer, $cs_1$, $cs_2$, $cs_3$, respectively, which corresponds to each of the differentiating metals, $m_1$, $m_2$, $m_3$ respectively. In the example shown in FIG. 4d, the same sensitive layer $cs_1$ is placed on all the transistors, independently of the differentiating metal.

The choice of metal/sensitive-layer pairs for each transistor of the array will essentially depend on the intended application and on a specific function of the sensitive layer. As regards preventing the NSB effect in an application for detecting a specific protein, typically in a liquid medium, the sensitive layer is chosen to promote the immobilization of this specific protein. It is therefore preferably the same for all the transistors of the array.

With regard to catalyzing a reaction with a gas molecule, it is possible to determine the optimum metal/sensitive-layer pair in terms of variation in electrical properties of the metal-channel junctions. There will therefore be several metal/sensitive-layer pairs determined for a detection array.

It should be noted that the sensitive layer must be exposed to the medium in which the detection takes place, at least around the junction or junctions of each transistor. This is a thin layer, so as to allow the nanotube element to act as transducer.

Thus, according to this aspect of the invention, a transistor may be differentiated from its neighbor by its electrode metal or by its sensitive layer placed on the nanotube. Many combinations may be produced by metal and polymer differentiations that use the same configurations: differentiation along rows, along columns, or 2D configurations, according to the performance expected, the type of analyte to be detected and the type of medium in which these analytes have to be detected.

As regards functionalization, this is achieved by the state-of-the-art techniques. In particular, when the functionalizing layer of the nanotube element is a layer of polymer, this may be deposited by spraying droplets.

An electronic analyte detection device 10 according to the invention therefore comprises at least one array R of transistors that are differentiated according to the invention and optionally functionalized.

A liquid or gaseous medium of defined composition therefore interacts in a differentiated manner with each of the transistors of the array of the device. It is thus possible to obtain a very specific imprint of this medium at a moment in question. This imprint may be defined by a matrix of conduction states of the transistors of the array R. The conduction state of a transistor is given by its threshold voltage, which varies according to the type of molecule to which the junction is exposed. Since the quantity of the molecules influences the intensity of the current passing through the transistors in the on-state, the conduction state is furthermore given by measuring the variation in transistor current with voltage $V_{gs}$.

Depending on the transistors of the array that are in the on-state for a given threshold voltage value and depending on the current signal (slope of the source-drain current $I_{ds}$ as a function of the gate-source voltage $V_{gs}$) passing through these transistors in the on-state, it is possible to deduce, respectively, the type of molecule which the nanotube-based transistors have been exposed and the quantity of molecules.

Depending on the intended application, in particular the type of analytes to be detected, the array is characterized by the choice of differentiating metals (depending on the technology adopted) and possibly of the sensitive functionalizing layer (or sensitive layers) that are appropriate for detecting these specific analytes. It is therefore possible to deduce the presence of these specific analytes and their concentration by appropriate electronic means for controlling and reading the transistors of the array.

Figure 6:
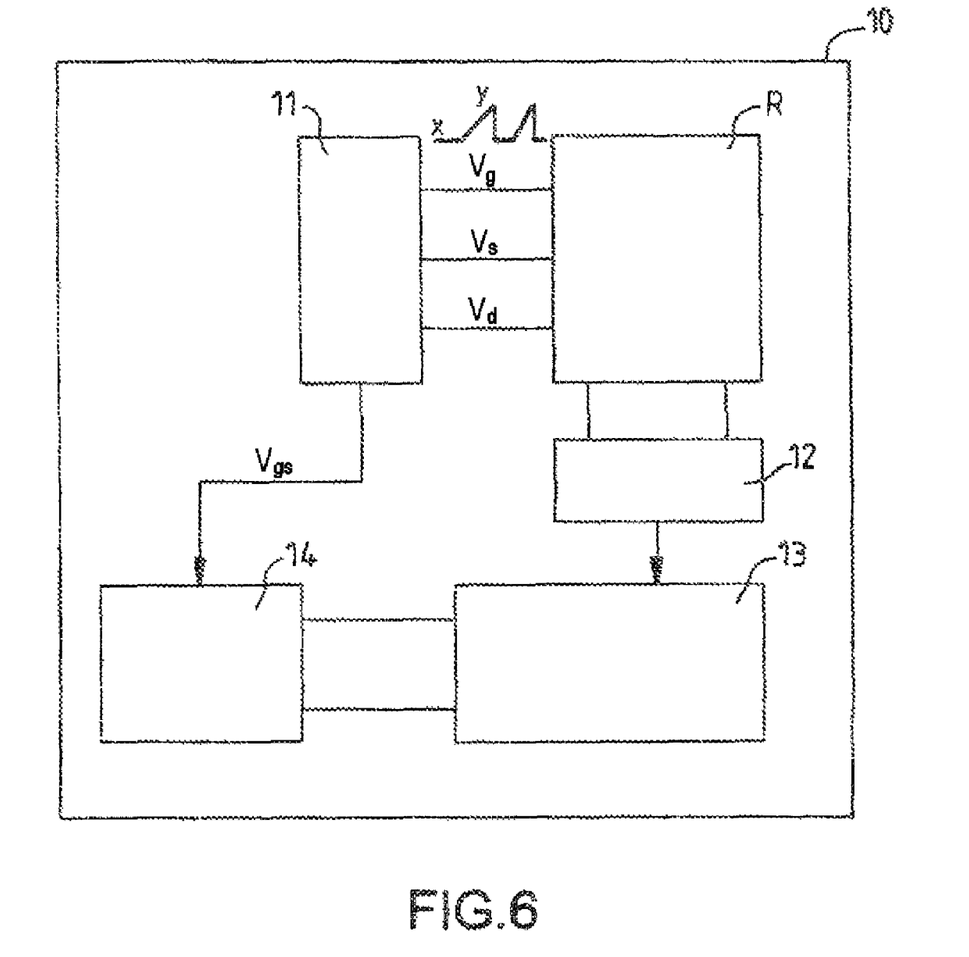
FIG. 6 is a block diagram of an electronic analyte detection device comprising an array according to the invention.

Typically and as illustrated schematically in FIG. 6, the electronic device 10 is provided with control means 11 for applying the gate voltage $V_g$ the drain voltage $V_d$ and the source voltage $V_s$ in an appropriate manner to the transistors of the array R and means 12 for reading the on-state (current-conducting state) or off-state of the transistors. These read means are associated with a memory 13 and data processing means 14, so as to be able to deduce therefrom, according to the voltage Vgs applied to each transistor of the array, the threshold voltage of each transistor. These processing means establish and analyze the matrix of conduction states thus obtained, in order to detect the presence of specific analytes.

This detection may be accomplished by comparison with one or more previous matrices.

Such detection may also be carried out relative to at least one reference matrix which is obtained by prior calibration and which constitutes the imprint on this array of the medium in which the detection takes place. This reference matrix is typically stored in the device 10 after a calibration step. This calibration step may consist of a recording of one or more matrices of conduction states of the transistors, under standard conditions of the medium to be monitored. These matrices are stored in the electronic device 10.

In operating mode, the matrix of conduction states of the matrix is periodically recorded. The matrix obtained is compared with each of the reference matrices in order to deduce the presence or absence of the specific analytes.

Figure 7A:
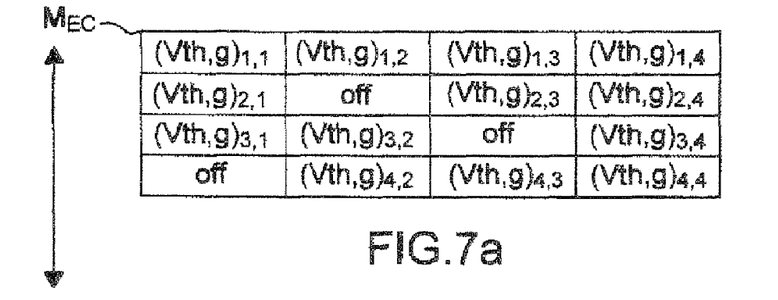
FIGS. 7a and 7b illustrate a matrix array R of differentiated and/or functionalized transistors according to the invention and a matrix Ec of measured conduction states for this array.
Figure 7B:
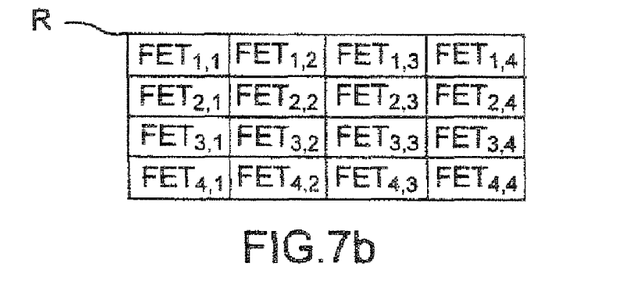

In the case of a positive detection of an analyte, the read means 12 furthermore advantageously allow the data processing means 14 to measure the slope g of the current $I_{ds}$ as a function of the gate-source voltage $V_{gs}$, so as to be able to deduce therefrom the concentration of the analytes detected. In FIGS. 7a and 7b, a matrix $M_{EC}$ of conduction states is shown schematically in FIG. 7a and matrix array R of transistors is indicated in FIG. 7b.

Corresponding to each transistor $FET_{i,j}$ of the array R is an off-state or an on-state. For the transistors in the on-state, the matrix $M_{EC}$ contains a (threshold voltage $V_{th}$/current slope g)$_{i,j}$ pair.

One procedure implemented by an electronic device 10 according to the invention may be the following, with an array R in which the transistors all receive the same gate voltage $V_g$, the same drain voltage $V_d$ and the same source voltage $V_s$:

a gate voltage signal $V_g$ that varies with time is applied as a voltage ramp from a value x to a value y, whereas the drain voltage $V_d$ and source voltage $V_s$ are fixed.

The values x and y of the voltage ramp $V_g$ are in practice chosen according to the characteristics of the transistors and to the intended application (characteristics of the medium or of the analyte(s) to be detected); and the read means 12 of determining the on-state or off-state of the transistors are configured with a detection threshold such that it is possible to clearly identify at which moment a transistor is in the on-state, taking into account the signal-to-noise ratio of the detection. In this regard, it should be noted that if the nanotube element NT of the transistors of the array comprises several nanotubes, the signal component is increased, thereby improving the detection.

By applying a voltage $V_g$ in the form of a ramp, it is possible, at each new ramp, to determine which transistors have been turned on and at which very precise gate voltages $V_g$.

These gate voltages at which the various transistors have been turned on make it possible to construct, for each ramp, a matrix of conduction states by which an analyte or analytes can be identified.

What is obtained is a real-time detection device, the response time of which is substantially equal to the duration of the ramp. It typically depends on the size of the array R and on the read time, and is therefore dependent on the technology of the transistors of the array and of the control/read means.

If it is desired to detect the intrusion of an analyte or analytes in a specific environment, such as an urban environment, an industrial environment, etc., a calibration step is necessary.

This calibration step consists firstly in testing the device 10 under conditions considered to be normal of the environment in question.

Taking for example a device for detecting sarin gas in a subway corridor, the various following steps may be provided:

Step 1: The matrix of conduction states of the transistors of the array R, placed in the environment in question, namely the "air" of the subway, is recorded.

Several calibration steps may be provided, depending on the presence of conventional pollutants ($NH_3$, $CO_2$, etc.) or "actual" concentrations (those which are normal in the environment in question) and/or according to a variable humidity concentration. For each calibration, the matrix of conduction states of the transistors of the array R is stored in memory. In practice, these conduction states are the values for activating the various transistors. What is obtained is one or more first reference matrices that are as many imprints that define the normality of the environment in question.

Step 2: The matrix of voltages for activating the transistors of the array R exposed to a variable concentration of sarin gas is recorded. This recording is made by simulating the usual environment, by varying the humidity and the concentration of the pollutants, as in step 1. Second reference matrices are obtained.

Step 3: The results are analyzed by comparing the first and second reference matrices. From this operation, the voltage or range of voltages for activating each transistor of the array so that it is possible to identify, unequivocally, the presence of sarin gas for various concentrations and for variable environmental parameters. What is obtained is a detection reference matrix with ranges of variation for each transistor.

Step 4: The device is placed in an operational environment. The matrix of voltages for activating the transistors of the array is periodically recorded, with an appropriate period, and this matrix is compared with the reference matrix determined in step 3. It is thus conceivable to compare this matrix recorded in operational mode with each of the reference matrices of step 2, according to the digital processing means available.

It should be noted that if the device is designed to detect several types of analyte, several steps 2 and 3 may be provided so as to construct, for each type, a detection reference matrix.

Various modes of use of the electronic detection device according to the invention may furthermore be provided.

In one mode of use as a mobile or portable device, the device is actuated manually by an operator who takes the recording. The portable device indicates any detection anomalies with respect to a normal situation.

In a mode of use in a "stationary" situation (for example a machine fixed to a wall), the device may be actuated automatically. For example, the device may be triggered every minute. The device takes its matrix recording and transmits it to a data processing center (for continuous monitoring).

In another mode of use, the machine is triggered remotely in the event of an alert, for example if a chemical alert is given. In this mode of use, the reality and the nature of the danger are checked.

In an embodiment particularly suitable for use of the detection device in an environment that may be very humid (but not liquid), for example in monsoon or tropical regions, a hot operation mode is provided, for example operating at a temperature of around 100° C. to 200° C., which can be obtained by a suitable heat air. In this way, the detection medium is "dried" locally, at least in the detection zone of the device, thereby making it possible to solve the problem of parasitic measurements according to the humidity. In this case, an array of differentiated transistors according to the invention, not functionalized by polymers, may be used.

It will be readily seen by one of ordinary skill in the art that the present invention fulfils all of the objects set forth above. After reading the foregoing specification, one of ordinary skill in the art will be able to affect various changes, substitutions of equivalents and various aspects of the invention as broadly disclosed herein. It is therefore intended that the protection granted hereon be limited only by the definition contained in the appended claims and equivalent thereof.

The invention claimed is:

1. An array of field-effect transistors for the detection of analytes, each transistor of the array comprising:
   a gate, a source electrode and a drain electrode, said electrodes being formed in a conducting material, and
   a nanotube or nanowire semiconductor element forming a channel of a transistor, said element being connected at one end to the source electrode and at the other end to the drain electrode, said source electrode, and said drain electrode, respectively forming with the channel a first junction and a second junction,
   wherein said array comprises at least two differentiated transistors,
   wherein a first of said at least two differentiated transistors has a source and a drain formed of a first material,
   wherein a second of said at least two differentiated transistors has a source and a drain formed of a second material,
   wherein said first material and said second material are different conductive materials,
   said transistors each including an exposed detection zone comprising one or both of said first and second junctions.

2. The array of transistors as claimed in claim 1, wherein:
   each junction is formed by a first and a second material having a contact surface in between, wherein
   one of first and second junctions of at least a first transistor, and a second transistor of the array are differentiated by the dimensions and/or shape of the contact surface between the first and second materials forming the junction, and wherein:
   the first and second materials forming the first junction respectively comprise the conducting material of the source and the conducting material of the nanotube semi-conductor element of the channel of the first junction, and the first and second materials forming the second junction respectively comprise the conducting material of the drain and the conducting material of the nanotube semi-conductor element of the channel of the second junction.

3. The array of transistors as claimed in claim 1, wherein at least said first junction formed with the source is exposed to the medium to be detected.

4. The array of transistors as claimed in claim 1, wherein at least one transistor of the array includes a sensitive functionalization layer deposited on the semiconductor element of said at least one transistor.

5. The array of transistors as claimed in claim 4, wherein said sensitive functionalization layer comprises a layer of polymer-type chemical molecules or enzymes.

6. The array of transistors as claimed in claim 4, wherein all or some of the transistors of the array include a sensitive functionalization layer and the type of the sensitive layer can vary depending on the transistor.

7. The array of transistors as claimed in claim 1, including a passivation layer with apertures corresponding to the detection zones of the array.

8. The array of transistors as claimed in claim 1, each transistor of the array comprising:
   a substrate forming a gate;
   a dielectric layer on the substrate; and
   a nanotube or nanowire semiconductor element, a source electrode and a drain electrode that are placed on the dielectric layer, the substrate forming the rear face, and said nanotube element, drain electrode and source electrode forming the active face.

9. The array as claimed in claim 8, comprising at least two subarrays of transistors and a support on which said subarrays are mounted.

10. The array as claimed in claim 9, wherein said subarrays are mounted on said support using the flip-chip technique.

11. The array as claimed in claim 10, including a passivation layer with apertures corresponding to the detection zones of the array; wherein said support includes conducting tracks for connecting the gate of each of said subarrays.

12. The array as claimed in claim 8, wherein the connection for the gate is provided in the active face via a hole etched in the dielectric layer.

13. The array of transistors as claimed in claim 1, wherein the conductive materials of the drain and source electrodes are respectively metal, and wherein a first transistor and a second transistor are differentiated in that the metal of the source electrode and/or the drain electrode of the first transistor is different from the metal of the source electrode and/or the drain electrode of the first transistor.

14. An electronic analyte detection device capable of operating in a liquid or gaseous medium, comprising:
an array of field-effect transistors as claimed in claim 1 and
control means for applying a gate voltage, a drain voltage and a source voltage to transistors of said array in order to determine, for each of said transistors, a threshold voltage corresponding to a gate-source voltage value at which said transistor is turned on,
means for storing a corresponding matrix of conduction states, which includes the threshold voltages for each of said transistors, and
data processing means for delivering detection information according to said matrix.

15. The electronic analyte detection device as claimed in claim 14, further including a heater for a hot operation mode.

16. The electronic analyte detection device as claimed in claim 14, wherein at least one of the transistors of the array is free of a sensitive functionalization layer deposited on the semiconductor element of said transistor.

17. The electronic detection device as claimed in claim 14, wherein:
said control means are configured so as to deliver a measure of the slope of the variation in current as a function of the reapplied gate-source voltage for each of said turned-on transistors,
the slopes of said transistors being stored in said matrix of conduction states, and
said data processing means being configured to deliver analyte concentration information on the basis of said slopes.

18. The electronic device as claimed in claim 14, wherein the data processing means comprise one or more reference matrices and comparison means for comparing a matrix of conduction states with said reference matrices.

19. The electronic analyte detection device as claimed in claim 14, wherein
the array of transistors is such that each junction is formed by a first and a second material having a contact surface in between, and wherein
one or both of first and second junctions of at least a first transistor and a second transistor of the array are differentiated by the dimensions and/or shape of the contact surface between the first and second materials forming the junction.

* * * * *